United States Patent [19]
Mabilat et al.

[11] Patent Number: 6,090,551
[45] Date of Patent: Jul. 18, 2000

[54] DETECTION OF BACTERIA OF GENUS LISTERIA USING NUCLEIC PROBE HYBRIDIZATION TECHNIQUES

[75] Inventors: Claude Mabilat, Rilleux-la-Pape; Brunehild Sallen, Lyons, both of France

[73] Assignee: Bio Merieux, Marcy l'Etoile, France

[21] Appl. No.: 08/875,296

[22] PCT Filed: Feb. 7, 1996

[86] PCT No.: PCT/FR96/00202

§ 371 Date: Sep. 29, 1997

§ 102(e) Date: Sep. 29, 1997

[87] PCT Pub. No.: WO96/24686

PCT Pub. Date: Aug. 15, 1996

[30] Foreign Application Priority Data

Feb. 8, 1995 [FR] France ................................. 95 01431

[51] Int. Cl.[7] .............................. C12Q 1/68; C12P 19/34; C07H 21/04
[52] U.S. Cl. .......................... 435/6; 435/91.2; 536/24.32; 536/24.33; 536/23.1
[58] Field of Search ............................... 435/6, 91.2, 810; 536/24.32, 24.33, 23.1; 935/8, 9, 78

[56] References Cited

U.S. PATENT DOCUMENTS

| | | | |
|---|---|---|---|
| 5,089,386 | 2/1992 | Stackebrandt et al. ..................... | 435/6 |
| 5,376,528 | 12/1994 | King et al. .................................. | 435/6 |

FOREIGN PATENT DOCUMENTS

| | | |
|---|---|---|
| 0297379 | 1/1989 | European Pat. Off. . |
| 0 314 294 | 5/1989 | European Pat. Off. . |
| 0 680 289 | 4/1992 | European Pat. Off. . |
| 0 501 356 | 9/1992 | European Pat. Off. . |
| 88/03957 | 6/1988 | WIPO . |
| WO 90/08841 | 8/1990 | WIPO . |
| WO 93 04201 | 3/1993 | WIPO . |
| WO 93/11257 | 6/1993 | WIPO . |
| WO 95/03412 | 2/1995 | WIPO . |

OTHER PUBLICATIONS

Baloga et al. Applied and Environmental Microbiology. 57: 2324–2331, Aug. 1991.

Smith et al. Methods in Enzymology. vol. 155, pp. 261–301, 1987.

Wang, Rong–Fu, et al., "Development of a 16S rRNA––Based Oligomer Probe Specific for *Listeria monocytogenes*", *Applied and Environmental Microbiology*, vol. 57, No. 12, Dec. 1991, pp. 3666–3670.

System, Appl. Microbiol. vol. 15, 487–501 (1992), "Complete 23S Ribosomal RNA Sequences of Gram–positive Bacteria with a Low DNA G+C Content", Wolfgang Lugwig et al.

FEMS Microbiology Letters 96 219–224 (1992), "Studies on the ribosomal RNA operons of *Listeria monocytogenes*", D.E. Thompson et al.

*Primary Examiner*—Carla J. Myers
*Attorney, Agent, or Firm*—Oliff & Berridge, PLC

[57] ABSTRACT

A single-stranded nucleotide fragment belonging to a variable region of the ribosomal RNA 23S of species of the genus mycobacterium. Probes and primers with sequences belonging to those of the single-stranded nucleotide fragments, a reagent and a method for identifying the mycobacterial species.

24 Claims, No Drawings

SEQUENCE LISTING (1) GENERAL INFORMATION:

(iii) NUMBER OF SEQUENCES: 75

(2) INFORMATION FOR SEQ ID NO:1:

(i) SEQUENCE CHARACTERISTICS:
       (A) LENGTH: 65 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

GGAGCCGTAG CGAAAGCGAG TCTGAATAGG GCGCATAAGT AACAGGTCGT AGACCCGAAA      60

CCAGG                                                                 65

(2) INFORMATION FOR SEQ ID NO:2:

(i) SEQUENCE CHARACTERISTICS:
       (A) LENGTH: 65 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

GGAGCCGTAG CGAAAGCGAG TCTGAATAGG GCGAATAAGT AACAGGTCGT AGACCCGAAA      60

CCAGG                                                                 65

(2) INFORMATION FOR SEQ ID NO:3:

(i) SEQUENCE CHARACTERISTICS:
       (A) LENGTH: 66 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

GGAGCCGTAG CGAAAGCGAG TCTGAATAGG GCGTATGAAG TAACAGGTCG TAGACCCGAA      60

ACCAGG                                                                66

(2) INFORMATION FOR SEQ ID NO:4:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

CCGAAACTGT GGATGAACCT CTTTAGAGGT TCGTGGTAGG AGAGCGTTCT AAGG           54

(2) INFORMATION FOR SEQ ID NO:5:

(i) SEQUENCE CHARACTERISTICS:
       (A) LENGTH: 64 base pairs
       (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:5:

AAACATATTA CCGAAACTGT GGATGAACCT CTTCGGAGGT TCGTGGTAGG AGAGCGTTCT     60

AAGG                                                                 64

(2) INFORMATION FOR SEQ ID NO:6:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AAACATATTA CCGAAACTGT GGATGAACCT CTTATAGAGG TTCGTGGTAG GAGAGCGTTC     60

TAAGG                                                                65

(2) INFORMATION FOR SEQ ID NO:7:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AAACGTATTA CCGAAACTGT GGATGAACAT CTTCGGATGT TCGTGGTAGG AGAGCGTTCT     60

AAGG                                                                 64

(2) INFORMATION FOR SEQ ID NO:8:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ACCCTGGCTG TATGACCATT CTAACCCGCC ACGCTTAGCG CGTGGGGAGA CAGTGTCAGG     60

TGGGCAG                                                              67

(2) INFORMATION FOR SEQ ID NO:9:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ACCCTGGCTG TATGACCATT CTAACCCACC ACGCTTAGCG CGTGGGGAGA CAGTGTCAGG     60

TGGGCAG                                                              67

(2) INFORMATION FOR SEQ ID NO:10:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
ACCCTGGCTG TATGACCATT CTAACCCGCC ACGCTAAGCG CGTGGGGAGA CAGTGTCAGG      60

TGGGCAG                                                                67
```

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
CCGAAACTGT GGATGAACCT CTTTAGAGGT TCGTGGTAGG                            40
```

(2) INFORMATION FOR SEQ ID NO:12:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
AGTCTGAATA GGGCGCATAA GTAACAGGTC GTAGA                                 35
```

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
AGTCTGAATA GGGCGAATAA GTAACAGGTC GTAGA                                 35
```

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
AGTCTGAATA GGGCGTATGA AGTAACAGGT CGTAGA                                36
```

(2) INFORMATION FOR SEQ ID NO:15:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:15:

CCGAAACTGT GGATGAACCT CTTTAGAGGT TCGTGGTAGG                40

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CCGAAACTGT GGATGAACCT CTTCGGAGGT TCGTGGTAGG                40

(2) INFORMATION FOR SEQ ID NO:17:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCGAAACTGT GGATGAACCT CTTATAGAGG TTCGTGGTAG G              41

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CCGAAACTGT GGATGAACAT CTTCGGATGT TCGTGGTAGG                40

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AAACGTATTA CCGAAACTGT GGATGAA                              27

(2) INFORMATION FOR SEQ ID NO:20:

(i) SEQUENCE CHARACTERISTICS:
        (A) LENGTH: 40 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:20:

CCGAAACTGT GGATGAACAT CTTCGGATGT TCGTGGTAGG                            40

(2) INFORMATION FOR SEQ ID NO:21:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TGGCTGTATG ACCATTCTAA CCCGCCACGC T                                     31

(2) INFORMATION FOR SEQ ID NO:22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CCACGCTTAG CGCGTGGGGA GACAGTGTCA GG                                    32

(2) INFORMATION FOR SEQ ID NO:23:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TGGCTGTATG ACCATTCTAA CCCACCACGC TTAGCGCGTG GGGAGACAGT GTCAGG          56

(2) INFORMATION FOR SEQ ID NO:24:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TGGCTGTATG ACCATTCTAA CCCGCCACGC TAAGCGCGTG GGGAGACAGT GTCAGG          56

(2) INFORMATION FOR SEQ ID NO:25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:25:

CCGCCACGCT TAGCGCGTGG GGAGACAGTG TCAGGTGGGC AG                              42

(2) INFORMATION FOR SEQ ID NO:26:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TGGCTGTATG ACCATTCTAA CCCGCCACGC TTAG                                      34

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GAATAGGGCG CATAAGTAAC A                                                    21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

GAATAGGGCG AATAAGTAAC A                                                    21

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

ATAGGGCGTA TGAAGTAACA                                                      20

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

TGAACCTCTT TAGAGGTTCG TG                                                   22

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TGAACCTCTT CGGAGGTTCG TG                                    22

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

TGAACCTCTT ATAGAGGTTC G                                     21

(2) INFORMATION FOR SEQ ID NO:33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GTGGATGAAC ATCTTCGGAT GTTCGTGGTA                           30

(2) INFORMATION FOR SEQ ID NO:34:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

AAACGTATTA CCGAA                                               15

(2) INFORMATION FOR SEQ ID NO:35:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

ATTCTAACCC GCCACGCT                                         18

(2) INFORMATION FOR SEQ ID NO:36:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:36:

ATTCTAACCC ACCACGCTTA G          21

(2) INFORMATION FOR SEQ ID NO:37:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

CCACGCTTAG CGCGTGGG          18

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CCGCCACGCT AAGCGCGTGG G          21

(2) INFORMATION FOR SEQ ID NO:39:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

CCGCCACGCT TAGCGCGTGG G          21

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

TTCTAACCCG CCACGCTTAG          20

(2) INFORMATION FOR SEQ ID NO:41:

(i) SEQUENCE CHARACTERISTICS:
        (A) LENGTH: 18 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:41:

AAGTAACAGG TCGTAGAC                                                18

(2) INFORMATION FOR SEQ ID NO:42:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:42:

TATTACCGAA ACTGTGGATG AAC                                          23

(2) INFORMATION FOR SEQ ID NO:43:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:43:

ACCCTGGCTG TATGACCATT CTAACCC                                      27

(2) INFORMATION FOR SEQ ID NO:44:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:44:

AGCGCGTGGG GAGACAGT                                                18

(2) INFORMATION FOR SEQ ID NO:45:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

CAGTGTCAGG TGGGCAG                                                 17

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:46:

GTTCGTGGTA GGAGAGCGTT                                           20

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

TCCGAATGGG GAAACCC                                              17

(2) INFORMATION FOR SEQ ID NO:48:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

GATCTGGGCT GTTTC                                                15

(2) INFORMATION FOR SEQ ID NO:49:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

AAGAGGGAAA CARCCCAGA                                            19

(2) INFORMATION FOR SEQ ID NO:50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

GGAACTTACC CGACAAGG                                             18

(2) INFORMATION FOR SEQ ID NO:51:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GAAATTCCTT GTCGGGT                                              17

(2) INFORMATION FOR SEQ ID NO:52:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

```
CTAGGTCTGA CCTATCAAT                                            19
```

(2) INFORMATION FOR SEQ ID NO:53:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
ACGAACCTCT AAAGAG                                               16
```

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
TAAGCGTGGC GGGTTAGAAT                                           20
```

(2) INFORMATION FOR SEQ ID NO:55:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

```
GGGTTAGAAT GGTCATACAG CCAGGGT                                   27
```

(2) INFORMATION FOR SEQ ID NO:56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

```
CCACGCGCTT AGCGTGG                                              17
```

(2) INFORMATION FOR SEQ ID NO:57:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

TTCATCCACA GTTTCGGTAA TATGT                                         25

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

CGAACCTCTA TAAGAGGTTC A                                             21

(2) INFORMATION FOR SEQ ID NO:59:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Listeria monocytogenes (vii) IMMEDIATE SOURCE:
        (A) LIBRARY: ATCC 19115

(xi) SEQUENCE DESCRIPTION: SEQ ID NO:59:

GGAGCCGTAG CGAAAGCGAG TCTGAATAGG GCGCATAAGT AACAGGTCGT AGACCCGAAA    60

CCAGG                                                               65

(2) INFORMATION FOR SEQ ID NO:60:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Listeria monocytogenes (vii) IMMEDIATE SOURCE:
        (A) LIBRARY: ATCC 19115

(xi) SEQUENCE DESCRIPTION: SEQ ID NO:60:

AAACATATTA CCGAAACTGT GGATGAACCT CTTTAGAGGT TCGTGGTAGG AGAGCGTTCT    60

AAGG                                                                64

(2) INFORMATION FOR SEQ ID NO:61:

(i) SEQUENCE CHARACTERISTICS:
        (A) LENGTH: 67 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
          (A) ORGANISM: Listeria monocytogenes (vii) IMMEDIATE SOURCE:
          (A) LIBRARY: ATCC 19115

(xi) SEQUENCE DESCRIPTION: SEQ ID NO:61:

ACCCTGGCTG TATGACCATT CTAACCCGCC ACGCTTAGCG CGTGGGGAGA CAGTGTCAGG      60

TGGGCAG                                                              67

(2) INFORMATION FOR SEQ ID NO:62:

(i) SEQUENCE CHARACTERISTICS:
          (A) LENGTH: 65 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Listeria seeligeri (vii) IMMEDIATE SOURCE:
          (A) LIBRARY: CCUG 15330

(xi) SEQUENCE DESCRIPTION: SEQ ID NO:62:

GGAGCCGTAG CGAAAGCGAG TCTGAATAGG GCGAATAAGT AACAGGTCGT AGACCCGAAA      60

CCAGG                                                                65

(2) INFORMATION FOR SEQ ID NO:63:

(i) SEQUENCE CHARACTERISTICS:
          (A) LENGTH: 67 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Listeria seeligeri (vii) IMMEDIATE SOURCE:
          (A) LIBRARY: CCUG 15330

(xi) SEQUENCE DESCRIPTION: SEQ ID NO:63:

ACCCTGGCTG TATGACCATT CTAACCCACC ACGCTTAGCG CGTGGGGAGA CAGTGTCAGG      60

TGGGCAG                                                              67

(2) INFORMATION FOR SEQ ID NO:64:

(i) SEQUENCE CHARACTERISTICS:
          (A) LENGTH: 65 base pairs
          (B) TYPE: nucleic acid
          (C) STRANDEDNESS: single
          (D) TOPOLOGY: linear (ii) MOLECULE TYPE: DNA (genomic)

(vi) ORIGINAL SOURCE:
          (A) ORGANISM: Listeria seeligeri
          (C) INDIVIDUAL ISOLATE: 8805029

(xi) SEQUENCE DESCRIPTION: SEQ ID NO:64:

```
GGANCCGTAG CGAAAGCGAG TCTGAATAGG GCGAATAAGT AACAGGTCGT AGACCCGAAA    60

CCAGG                                                                65
```

(2) INFORMATION FOR SEQ ID NO:65:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Listeria innocua (vii) IMMEDIATE SOURCE:
        (A) LIBRARY: ATCC 33090

(xi) SEQUENCE DESCRIPTION: SEQ ID NO:65:

```
AAACATATTA CCGAAACTGT GGATGAACCT CTTCGGAGGT TCGTGGTAGG AGAGCGTTCT    60

AAGG                                                                 64
```

(2) INFORMATION FOR SEQ ID NO:66:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Listeria innocua (vii) IMMEDIATE SOURCE:
        (A) LIBRARY: ATCC 33090

(xi) SEQUENCE DESCRIPTION: SEQ ID NO:66:

```
ACCCTGGCTG TATGACCATT CTAACCCGCC ACGCTAAGCG CGTGGGGAGA CAGTGTCAGG    60

TGGGCAG                                                              67
```

(2) INFORMATION FOR SEQ ID NO:67:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Listeria ivanovii
        (C) INDIVIDUAL ISOLATE: 8805019

(xi) SEQUENCE DESCRIPTION: SEQ ID NO:67:

```
AAACATATTA CCGAAACTGT GGATGAACCT CTTATAGAGG TTCGTGGTAG GAGAGCGTTC    60

TAAGG                                                                65
```

(2) INFORMATION FOR SEQ ID NO:68:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: Listeria grayi (vii) IMMEDIATE SOURCE:
            (A) LIBRARY: ATCC 19120

(xi) SEQUENCE DESCRIPTION: SEQ ID NO:68:

GGAGCCGTAG CGAAAGCGAG TCTGAATAGG GCGTATGAAG TAACAGGTCG TAGACCCGAA       60

ACCAGG      66

(2) INFORMATION FOR SEQ ID NO:69:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Listeria grayi (vii) IMMEDIATE SOURCE:
            (A) LIBRARY: ATCC 19120

(xi) SEQUENCE DESCRIPTION: SEQ ID NO:69:

AAACGTATTA CCGAAACTGT GGATGAACAT CTTCGGATGT TCGTGGTAGG AGAGCGTTCT       60

AAGG      64

(2) INFORMATION FOR SEQ ID NO:70:

(i) SEQUENCE CHARACTERISTICS:
            (A) LENGTH: 64 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Brochothrix campestris (vii) IMMEDIATE SOURCE:
            (A) LIBRARY: ATCC 43754

(xi) SEQUENCE DESCRIPTION: SEQ ID NO:70:

GGAGCCGTAG CGAAAGCGAG TCTGAATAGG GCGTATAGTA TTTGGTCGTA GACCCGAAGC       60

CAGG      64

(2) INFORMATION FOR SEQ ID NO:71:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Brochothrix campestris (vii) IMMEDIATE SOURCE:
            (A) LIBRARY: ATCC 43754

(xi) SEQUENCE DESCRIPTION: SEQ ID NO:71:

AAACATATTA CCGAAGCTGT GGATTGTCCT TTGGACAATG GTAGGAGAGC GTTCTAAGG        59

(2) INFORMATION FOR SEQ ID NO:72:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: B. campestris (vii) IMMEDIATE SOURCE:
        (A) LIBRARY: ATCC 43754

(xi) SEQUENCE DESCRIPTION: SEQ ID NO:72:

ACCCTAGCTG TGTTGGCTTT CTAACCCGCA CCACTTATCG TGGTGGGAGA CAGTGTCAGG        60

CGGGCAG        67

(2) INFORMATION FOR SEQ ID NO:73:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Brochothrix thermosphacta (vii) IMMEDIATE SOURCE:
        (A) LIBRARY: ATCC 11509

(xi) SEQUENCE DESCRIPTION: SEQ ID NO:73:

GGAGCCGTAG CGAAAGCGAG TCTGAATAGG GCGTTTAGTA TTTGGTCGTA GACCCGAAAC        60

CAGG        64

(2) INFORMATION FOR SEQ ID NO:74:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: B. thermosphacta (vii) IMMEDIATE SOURCE:
        (A) LIBRARY: ATCC 11509

(xi) SEQUENCE DESCRIPTION: SEQ ID NO:74:

AAACATATTA CCGAAGCTGT GGATTGTCCG TAGGACAATG GTAGGAGAGC GTTCTAAGG        59

(2) INFORMATION FOR SEQ ID NO:75:

(i) SEQUENCE CHARACTERISTICS:
        (A) LENGTH: 67 base pairs
        (B) TYPE: nucleic acid
        (C) STRANDEDNESS: single
        (D) TOPOLOGY: linear -continued

```
    (ii) MOLECULE TYPE: DNA (genomic)

(vi) ORIGINAL SOURCE:
         (A) ORGANISM: B. thermosphacta (vii) IMMEDIATE SOURCE:
         (A) LIBRARY: ATCC 11509

(xi) SEQUENCE DESCRIPTION: SEQ ID NO:75:

ACCCTAGCTG TGTTGGCTTT CTAACCCGCA CCACTTATCG TGGTGGGAGA CAGTGTCAGG        60

TGGGCAG                                                                 67
```

DETECTION OF BACTERIA OF GENUS LISTERIA USING NUCLEIC PROBE HYBRIDIZATION TECHNIQUES

The present invention relates to the field of detection and/or amplification techniques using oligonucleotide probes or primers, and to their application in testing for the presence or in the identification of bacteria of the genus Listeria.

Listeria are Gram + bacteria belonging to the Listeriaceae family which is subdivided into two genera: the genus Listeria and the genus Brochothrix (Collins et al., 1991, International Journal of Systematic Bacteriology, 41, 240–246). The genus Listeria groups together the following bacterial species: *Listeria monocytogenes, Listeria innocua, Listeria seeligeri, Listeria welshimeri, Listeria ivanovii, Listeria murrayi* and *Listeria grayi*. Only the *Lysteria monocytogenes* species exhibits pathogenicity for man. This species is in particular responsible, in man, for severe pathologies such as meningoencephalites, septicemias or abortions. Moreover, since 1981, the *Listeria monocytogenes* species has been recognized as the agent responsible for several food intoxication epidemics especially in Canada in 1981, in the United States from 1983 to 1985, in Switzerland from 1983 to 1987 and very recently in France in 1992 and 1993. The mortality rate associated with these epidemics is very high, about a third of the cases resulting in abortion or death.

It is therefore important to develop a bacteriological diagnostic test which is sufficiently specific and sensitive to allow rapid and selective detection of the *Listeria monocytogenes* species, which can be used in particular in the food industry and in medical diagnostics.

A first generation of rapid tests has been proposed, based on the flow cytometry technique (Donnelly C. W., G. J. Baigent, and E. H. Briggs, 1988: Flow cytometry for automated analysis of milk containing *Listeria monocytogenes*; J. Assoc. Off. Anal. Chem. 71: 655–658) or on the ELISA (enzyme-linked immunosorbent assay) method (Mattingley J. A., B. T. Butman, M. C. Planck, R. J. Durham, and B. J. Robinson, 1988: Rapid monoclonal antibody-based enzyme-linked 4imunosorbent assay for the detection of Listeria in food products; J. Assoc. Off. Anal. Chem. 71: 679–681). However, these techniques allow only the detection of bacteria belonging to the genus Listeria without any discrimination between the species, and in particular the pathogenic species *Listeria monocytogenes*.

Other techniques of detection by nucleic acid hybridization, using genetic markers, were then developed. It has thus been shown that certain nucleic acid sequences are specific for the sole *L. monocytogenes* species. These sequences form in particular part of the genes encoding determinants of virulence, such as the region downstream of the hlyA gene (listeriolysin O) (Mengaud J., M. F. Vicente, J. Chenevert, J. Moniz-Pereira, C. Geoffroy, B. Gicquel-Sanzey, F. Baquero, J. C. Perez-Diaz, and P. Cossart, 1988: Expression in *Escherichia coli* and sequence analysis of the listeriolysin O determinant of *Listeria monocytogenes*; Infect. Immun. 56: 766–772) or the iap gene (invasion-associated protein, also called p60, Köhler S., M. Leimeister-Wächter, T. Chakraborty, F. Lottspeich, and W. Goebel, 1990: The gene coding for protein p60 of *Listeria monocytogenes* and its use as a specific probe for *Listeria monocytogenes*; Infect. Immun. 58: 1943–1950). However, the use of these markers requires a preliminary step of nucleic acid amplification in order to obtain an appropriate sensitivity of the tests, because each of these genes is only present in a single copy.

The present invention overcomes the disadvantages cited above for the detection of the presence of bacteria of the genus Listeria, and more particularly of the species *Listeria monocytogenes*, using a genetic marker in a process of detection by nucleic acid hybridization combining specificity, sensitivity and speed.

Bacterial ribosomes contain at least three distinct RNA molecules called 5S, 16S and 23S rRNA. Historically, these names were chosen with reference to their speed of sedimentation which is linked to the size of these RNA molecules.

In the process of the invention, the ribosomal RNA (rRNA) of the bacteria may be used as target. One of the advantages of this use is that the rRNA is found in abundance in all the cells of living organisms.

The use of the Listeria 16S rRNA in the diagnosis of listerioses has been described (see especially Wang R.-F. et al., 1991: Development of a 16S rRNA-based oligomer probe specific for *Listeria monocytogenes*; Appl. Environ. Microbiol. 57:3666–3670, patent applications No. EP 314 294, No. WO 90/0884 and U.S. Pat. No. 5,089,386).

There have now been discovered on the DNA encoding the ribosomal RNA of the 23S subunit zones which are variable depending on the bacterial genera, but which appear to be conserved among the species belonging to the Listeria genus, which makes it possible to discriminate at least one group of species of the genus Listeria from other bacterial genera or groups of genera. Moreover, minor sequence variations exist between the said species in the said conserved zones among the species of the genus Listeria. These different results have made it possible to design nucleic probes which are specific for species or for groups of species of Listeria.

Before disclosing the invention in greater detail, various terms used in the description and the claims are defined below:

"nucleic acid extracted from bacteria" is understood to mean either the total nucleic acid or the ribosomal RNA, in particular the 23S rRNA, or the genomic DNA, or alternatively a DNA obtained from the reverse transcription of the 23S ribosomal RNA, a "nucleotide fragment" or an "oligonucleotide" are two synonymous terms designating a chain of nucleotide units characterized by the informational sequence of the natural (or optionally modified) nucleic acids and which are capable of hybridizing, like the natural nucleic acids, with a complimentary or substantially complimentary nucleotide fragment, under predetermined conditions. The chain may contain nucleotide units of different structure from that of the natural nucleic acids. A nucleotide fragment (or oligonucleotide) may contain, for example, up to 100 nucleotide units. It generally contains at least 10, and in particular at least 12 nucleotide units and may be obtained from a natural nucleic acid molecule and/or by genetic recombination and/or by chemical synthesis, a nucleotide unit is derived from a monomer which may be a natural nucleotide of nucleic acid in which the constituent components are a sugar, a phosphate group and a nitrogen base; in DNA, the sugar is 2-deoxyribose in RNA, the sugar is ribose; depending on whether DNA or RNA is involved, the nitrogen base is chosen from adenine, guanine, uracil, cytosine, thymine; or the monomer is a nucleotide modified in at least one of the three constituent components; by way of example, the modification may occur either at the level of the bases, with modified bases such as inosine, 5-methyl-deoxycytidine, deoxyuridine, 5-dimethylaminodeoxyuridine, 2,6-diaminopurine, 5-bromodeoxyuridine or any other modified base capable of hybridization, or at the level of the sugar, for example the replacement of at least one deoxyribose with a polyamide (P. E. Nielsen et al., Science, 254, 1497–1500 (1991), or alternatively at the level of the phosphate group, for example its replacement with esters in particular chosen from diphosphates, alkyl- and aryl-phosphonates and phosphorothioates, "informational sequence" is understood to mean any orderly succession of nucleotide-type units, whose chemical nature and order in a reference direction constitutes an information analogous to that given by the sequence of natural nucleic acids, "hybridization" is understood to mean the procedure during which, under appropriate conditions, two nucleotide fragments having sufficiently complimentary sequences are capable of combining through stable and specific hydrogen bonds to form a double strand. The hybridization conditions are determined by the "stringency", that is to say the severity of the operating conditions. The higher the stringency at which it is performed, the more specific the hybridization. The stringency is a function in particular of the base composition of a probe/target duplex, as well as the degree of mismatch between two nucleic acids. The stringency may also be a function of the hybridization reaction parameters such as the concentration and the type of ionic species present in the hybridization solution, the nature and the concentration of denaturing agents and/ or the hybridization temperature. The stringency of the conditions under which a hybridization reaction should be carried out depends in particular on the probes used. All these data are well known and the appropriate conditions may be possibly determined in each case by routine experiments. In general, depending on the length of the probes used, the temperature for the hybridization reaction is between about 20 and 65° C., in particular between 35 and 65° C. in a saline solution at a concentration of about 0.8 to 1 M, a "probe" is a nucleotide fragment comprising, for example, from 10 to 100 nucleotide units, in particular from 12 to 35 nucleotide units, having a hybridization specificity under determined conditions to form a hybridization complex with a target nucleic acid having, in the present case, a nucleotide sequence included either in a ribosomal RNA, or in a DNA obtained by reverse transcription of the said ribosomal RNA, or alternatively in a DNA (called here ribosomal DNA or rDNA) of which the said ribosomal RNA is the product of transcription; a probe may be used for diagnostic purposes (in particular capture or detection probes) or for therapeutic purposes, a "capture probe" is immobilized or can be immobilized on a solid support by any appropriate means, for example by covalent bonding, by adsorption, or by direct synthesis on a solid support (see in particular patent application WO 92 10092), a "detection probe" may be labelled by means of a marker chosen, for example, from radioactive isotopes, enzymes, in particular enzymes capable of acting on a chromogenic, fluorigenic or luminescent substrate (in particular a peroxidase or an alkaline phosphatase), chromophoric chemical compounds, chromogenic, fluorigenic or luminescent compounds, analogues of nucleotide bases, and ligands such as biotin, a "primer" is a probe comprising, for example, from 10 to 100 nucleotide units and having a hybridization specificity under determined conditions for the initiation of an enzymatic polymerization, for example in an amplification technique such as PCR (Polymerase Chain Reaction), in a process of sequencing, in a method of reverse transcription and the like.

The probes according to the invention may be used, for diagnostic purposes, in testing for the presence or for the absence of a target nucleic acid in a sample, according to all the hybridization techniques known and in particular the techniques of point deposition on filter, termed "dot-blot" (MANIATIS et al., Molecular Cloning, Cold Spring Harbor, 1982), the techniques of DNA transfer, termed "Southern blot" (SOUTHERN. E. M., J. Mol. Biol., 98, 503 (1975), the techniques of RNA transfer, termed "Northern blot", or the so-called "sandwich" techniques (DUNN A. R., HASSEL J. A., Cell, 12, 23 (1977)); the sandwich technique in particular is used with a capture probe and/or a detection probe, the said probes being capable of hybridizing with two different regions of the target nucleic acid, and at least one of the said probes (generally the detection probe) being capable of hybridizing with a region of the target which is specific for the desired species or group of species, it being understood that the capture probe and the detection probe should have nucleotide sequences which are at least partially different.

Under the conditions which are specified in Example 1 below, the nucleotide sequence of the rDNA corresponding to the 23S ribosomal RNA of two species of Listeria, as well as of a species of the phylogenetic genus immediately close to that of Listeria, namely the genus Brochothrix, was determined. This study related to the species *L. monocytogenes, L. innocua* and *Brochothrix thermosphacta.*

Highly conserved regions were sought for the sole Listeria genus, which makes it possible to distinguish other bacterial genera, as well as variable regions within the genus Listeria, and which therefore make it possible to distinguish several species or groups of species of Listeria. Three advantageous regions, namely 664–728, 1188–1251 and 2209–2275 were thus selected with reference to the numbering of the nucleotide sequence of the 23S rRNA of *Listeria monocytogenes* ATCC 19115. The sequences of these same regions were determined for various strains of other species of Listeria as well as for the species *Brochothrix campestris*. The results of these various sequencings are summarized in the table of sequences presented in Table 1–3. In the sequences in the table, the sign * represents a vacant site whose representation is necessary for the alignment of the sequences, taking into consideration certain species having an additional nucleotide unit at this site.

The results of these searches, that is to say the alignments of sequences presented in Table 1–3, made it possible to design probes which make it possible to detect groups of species or to identify certain species of the genus Listeria. By choosing probes in the regions conserved in all the species of Listeria, it is possible to detect the presence or the absence of at least any bacterium of the genus Listeria. By using probes containing mutated zones for a particular species (compared with the reference species, here *L. monocytogenes*), it is possible to detect directly the presence of such a species. In the sandwich hybridization techniques, using two probes in combination (capture probe and detection probe), a probe specific for the genus Listeria and a probe specific for the species considered will be used, for example, in combination. It is also possible to use in combination two probes specific for the said species, when they exist, these two probes being complementary to the non-overlapping regions of the 23S rRNA of the said species.

In other cases (in particular for *Listeria monocytogenes*), there is no single probe allowing direct characterization of a given species. It is then possible to use two probes in combination (in particular according to the sandwich hybridization technique), namely, for example: on the one hand, a first probe allowing the hybridization with the rRNA (or the rDNA) of *Listeria monocytogenes* and of a second species of Listeria, and on the other hand, a second probe capable of hybridizing with the rRNA or rDNA of *Listeria monocytogenes* and of one or more other species of Listeria but not of the said second species. If hybridization of the nucleic acid of the sample with such a system of two probes is observed, it is possible to conclude as to the presence of *Listeria monocytogenes*.

As indicated above, the nucleotide probes of the invention may be used in conventional methods of hybridization. The nucleic acid to be detected (target) may be DNA (optionally obtained after amplification) or RNA. In the case of a double-stranded nucleic target, it is advisable to carry out its denaturation before carrying out the process of detection. The target nucleic acid may be obtained by extraction, according to known methods, of the nucleic acids from a sample to be examined. The denaturation of a double-stranded nucleic acid may be carried out by known methods of chemical, physical or enzymatic denaturation, and in particular by heating at an appropriate temperature, greater than 80° C.

In some cases, the detection of the presence of a given species of Listeria requires the use of probes allowing the detection of a point mutation. For that, it is advisable to carry out the operations with probes of a predetermined length (number of nucleotide units), under conditions which are themselves predetermined. Other items of specific information are given below, with reference more particularly to the sandwich hybridization method which constitutes one of the hybridization methods most frequently used currently. This method comprises the contacting of a first probe attached to a solid support with a solution containing the nucleic acid to be analysed, and the contacting of the said support with the detection probe, the incubation of the mixture obtained, the rinsing of the support in order to remove the constituents not attached to the support by specific hybridization and the qualitative or quantitative detection, using a reaction for revealing the marker attached to the support, of the detection probe attached. The revealing of the presence of the marker may be carried out, for example, by colorimetry, fluorescence or luminescence. The contacting of the capture probe with the sample and with the detection probe may be carried out sequentially, optionally with intermediate rinsing of the support. The operation may also be carried out by simultaneous or practically simultaneous contacting of the capture probe attached to the support with a solution containing the sample and the detection probe which may be added in the form of a mixture or separately.

The incubation and subsequent washing stages which constitute the key stages of the sandwich hybridization process are each carried out at a constant temperature which may be, for example, between the range mentioned above (see the "Definitions"). It is known that nucleic acid hybrids have a dissociation temperature which depends on the number of hybridized bases (the temperature increasing with the size of the hybrid) and which also depends on the nature of the hybridized bases and, for each hybridized base, on the nature of the adjacent bases. The dissociation of the hybrids occurs in a temperature range of a few degrees and may be easily determined, for example, by UV spectroscopy. It is possible to determine experimentally the half-dissociation temperature of the hybrid formed by a given probe with the target of complementary sequence, by simple routine experiment. The hybridization temperature used in the sandwich hybridization technique should obviously be chosen below the half-dissociation temperature. More precisely, the operation is carried out at a temperature less than the half-dissociation temperature of the least stable hybrid among the two hybrids which the target forms with, on the one hand, the capture probe and, on the other hand, the detection probe, so that the two hybrids are stable at the temperature at which the operation is carried out. A point mutation, that is to say a mutation causing a mismatch affecting a single base pair in the hybrid, causes a modification, generally a reduction, of the half-dissociation temperature. By using sufficiently short probes, such a single mismatch may cause a relatively high reduction in the half-dissociation temperature, of the order of a few degrees. Thus, by choosing, using preliminary routine experiments, a probe of appropriate length, by carrying out the procedure in a given buffer solution, it is possible to determine a temperature at which it will be possible to observe the hybridization only in the case where the probe is strictly complementary to the target. In addition, through the choice of short probes of predetermined length, it is possible to use the sandwich hybridization technique at a single predetermined temperature, for example 37° C. For a more detailed discussion of the sandwich hybridization technique with the use of short probes, reference may be made in particular to patent application FR-2,663,040.

The subject of the invention is therefore a single-stranded oligonucleotide, characterized in that it is chosen from the oligonucleotides, having at least 12 nucleotide units, whose sequence is included in one of the sequences ($a_1$) to ($a_{10}$) of the following listing:

(a₁) GGAGCCGTAG CGAAAGCGAG TCTGAATAGG GCGCATAAGT AACAGGTCGT
      AGACCCGAAA CCAGG (SEQ ID NO:1)
(a₂) GGAGCCGTAG CGAAAGCGAG TCTGAATAGG GCGAATAAGT AACAGGTCGT
      AGACCCGAAA CCAGG (SEQ ID NO:2)
(a₃) GGAGCCGTAG CGAAAGCGAG TCTGAATAGG GCGTATGAAG TAACAGGTCG
      TAGACCCGAA ACCAGG (SEQ ID NO:3)
(a₄) CCGAAACTGT GGATGAACCT CTTTAGAGGT TCGTGGTAGG AGAGCGTTCT
      AAGG (SEQ ID NO:4)
(a₅) AAACATATTA CCGAAACTGT GGATGAACCT CTTCGGAGGT TCGTGGTAGG
      AGAGCGTTCT AAGG (SEQ ID NO:5)
(a₆) AAACATATTA CCGAAACTGT GGATGAACCT CTTATAGAGG TTCGTGGTAG
      GAGAGCGTTC TAAGG (SEQ ID NO:6)
(a₇) AAACGTATTA CCGAAACTGT GGATGAACAT CTTCGGATGT TCGTGGTAGG
      AGAGCGTTCT AAGG (SEQ ID NO:7)
(a₈) ACCCTGGCTG TATGACCATT CTAACCCGCC ACGCTTAGCG CGTGGGGAGA
      CAGTGTCAGG TGGGCAG (SEQ ID NO:8)
(a₉) ACCCTGGCTG TATGACCATT CTAACCCACC ACGCTTAGCG CGTGGGGAGA
      CAGTGTCAGG TGGGCAG (SEQ ID NO:9)
(a₁₀) ACCCTGGCTG TATGACCATT CTAACCCGCC ACGCTAAGCG CGTGGGGAGA
      CAGTGTCAGG TGGGCAG (SEQ ID NO:10);

as well as an oligonucleotide complementary to the said oligonucleotide.

Among the oligonucleotides of the invention whose sequence is included in the sequence (a₄), there may be mentioned in particular those whose sequence is included in the sequence (a'₄):

(a'₄) CCGAAACTGT GGATGAACCT CTTTAGAGGT TCGTGGTAGG (SEQ ID NO:11)

Among the oligonucleotides of the invention, some may be used to characterize a species or a group of species of the genus Listeria. They are in particular the oligonucleotides defined by means of the sequences (b₁) to (b₁₅) and (c₁) to (c₁₄) below.

The invention relates in particular to an oligonucleotide as defined above, characterized in that it comprises a sequence of at least five consecutive nucleotide units included in a sequence between the square brackets in sequences (b₁) to (b₁₅) of the following listing:

(b₁)  AGTCTGAATA  GG[GCGCATA]A  GTAACAGGTC  GTAGA (SEQ ID NO:12)
(b₂)  AGTCTGAATA  GG[GCGAATA]A  GTAACAGGTC  GTAGA (SEQ ID NO:13)
(b₃)  AGTCTGAATA  GG[GCGTATGA  AG]TAACAGGT  CGTAGA (SEQ ID NO:14)
(b₄)  CCGAAACTGT  GGATGAACCT  [CTTTAGAG]GT  TCGTGGTAGG (SEQ ID NO:15)
(b₅)  CCGAAACTGT  GGATGAACCT  [CTTCGGAG]GT  TCGTGGTAGG (SEQ ID NO:16)
(b₆)  CCGAAACTGT  GGATGAACCT  [CTTATAG]AGG  TTCGTGGTAG  G (SEQ ID NO:17)
(b₇)  CCGAAACTGT  GGATGAACAT  CTT[CGGATGT  T]CGTGGTAGG (SEQ ID NO:18)
(b₈)  A[AACGTAT]TA  CCGAAACTGT  GGATGAA (SEQ ID NO:19)
(b₉)  CCGAAACTGT  GGATG[AACAT  CT]TCGGATGT  TCGTGGTAGG (SEQ ID NO:20)
(b₁₀) TGGCTGTATG  ACCATTCTAA  [CCCGCCA]CGC  T (SEQ ID NO:21)
(b₁₁) CCAC[GCTTAG  C]GCGTGGGGA  GACAGTGTCA  GG (SEQ ID NO:22)
(b₁₂) TGGCTGTATG  ACCATTCTAA  [CCCACCA]CGC  TTAGCGCGTG
      GGGAGACAGT  GTCAGG (SEQ ID NO:23)
(b₁₃) TGGCTGTATG  ACCATTCTAA  CCCGCCAC[GC  TAAGC]GCGTG
      GGGAGACAGT  GTCAGG (SEQ ID NO:24)
(b₁₄) [CCGCCA]CGCT  TAGCGCGTGG  GGAGACAGTG  TCAGGTGGGC  AG (SEQ ID NO:25)
(b₁₅) TGGCTGTATG  ACCATTCTAA  CCCGCCAC[GC  TTAG] (SEQ ID NO:26);

as well as an oligonucleotide complementary to the said oligonucleotide.

(c₁) GAATAGGGCG CATAAGTAAC A (SEQ ID NO:27)
(c₂) GAATAGGGCG AATAAGTAAC A (SEQ ID NO:28)
(c₃) ATAGGGCGTA TGAAGTAACA (SEQ ID NO:29)
(c₄) TGAACCTCTT TAGAGGTTCG TG (SEQ ID NO:30)
(c₅) TGAACCTCTT CGGAGGTTCG TG (SEQ ID NO:31)
(c₆) TGAACCTCTT ATAGAGGTTC G (SEQ ID NO:32)

```
                           -continued
(c₇)    GTGGATGAAC ATCTTCGGAT  GTTCGTGGTA (SEQ ID NO:33)
(c₈)    AAACGTATTA CCGAA (SEQ ID NO:34)
(c₉)    ATTCTAACCC GCCACGCT (SEQ ID NO:35)
(c₁₀)   ATTCTAACCC ACCACGCTTA  G (SEQ ID NO:36)
(c₁₁)   CCACGCTTAG CGCGTGG     G (SEQ ID NO:37)
(c₁₂)   CCGCCACGCT AAGCGCGTGG  G (SEQ ID NO:38)
(c₁₃)   CCGCCACGCT TAGCGCGTGG  G (SEQ ID NO:39)
(c₁₄)   TTCTAACCCG CCACGCTTAG (SEQ ID NO:40);
``` as well as an oligonucleotide complementary to the said nucleotide.

Among the oligonucleotides of the invention, some can be used as a probe allowing the detection of any bacterium of the genus Listeria. They are in particular the oligonucleotides defined by means of the sequences ($d_1$) to ($d_6$) below.

The subject of the invention is therefore also an oligonucleotide as defined above, characterized in that its sequence is included in one of the following sequences ($d_1$) to ($d_6$):

```
(d₁)    AAGTAACAGG TCGTAGAC (SEQ ID NO:41)
(d₂)    TATTACCGAA ACTGTGGATG  AAC (SEQ ID NO:42)
(d₃)    ACCCTGGCTG TATGACCATT  CTAACCC (SEQ ID NO:43)
(d₄)    AGCGCGTGGG GAGACAGT (SEQ ID NO:44)
(d₅)    CAGTGTCAGG TGGGCAG (SEQ ID NO:45)
(d₆)    GTTCGTGGTA GGAGAGCGTT (SEQ ID NO:46).
```

For use in conventional hybridization techniques, the oligonucleotides of the invention may be immobilized on a solid support (this is in particular the case for a capture probe) or labelled with a tracer (detection probe).

The subject of the invention is also a process for determining the presence or absence of at least one bacterium of the genus Listeria, in a sample containing or capable of containing nucleic acids of at least one such bacterium, according to a method in which the said sample is contacted with at least one nucleic probe, then the formation or the absence of formation of a hybridization complex between the said probe and the nucleic acid of the sample is determined in a manner known per se, characterized in that the said probe is an oligonucleotide chosen from those which have been defined above.

For the determination of the presence or absence of a species or group of species of bacterium of the genus Listeria, it is possible to use as nucleic probes, on the one hand, a first probe as defined above and, on the other hand, a probe as defined by one of the sequences ($b_1$) to ($b_{15}$) or ($c_1$) to ($c_{14}$), it being understood that the said first and second probes are capable of hybridizing with non-overlapping regions of the 23S rRNA (or its complementary) of a bacterium of the genus Listeria. The first probe is for example immobilized on a solid support and the second probe is labelled with a tracer. To determine the presence or absence of at least (any) one bacterium of the genus Listeria, it is possible to use as probe at least one oligonucleotide as defined by the sequences ($d_1$) to ($d_6$).

It is possible to detect the presence of certain bacteria of the genus Listeria, optionally with a single probe, for example:

Listeria seeligeri: probe included in the sequence ($b_2$), ($b_{12}$), ($c_2$) or ($c_{10}$);

Listeria innocua: probe included in the sequence ($b_{13}$) or ($c_{12}$);

Listeria ivanovii: probe included in the sequence ($b_6$) or ($c_6$);

Listeria grayi and/or Listeria murrayi (these two species not being distinguishable by means of the probes of the invention): probe included in the sequence ($b_3$), ($b_7$), ($b_8$), ($b_9$), ($c_3$), ($c_7$) or ($c_8$).

When it is desired to use a probe which is derived from annex ⅓, for the determination of a particular species, it is advisable to check beforehand, using the probes ($b_6$) or ($c_6$), if Listeria ivanovii is present. If so, it is not possible to use a probe derived from annex Table 1 for the determination envisaged (because the sequence corresponding to annex Table 1 has not been determined for L. ivanovii).

When a system with two probes is used, it is possible to use, in order to determine the bacteria which have just been mentioned, on the one hand, a probe specific for the genus Listeria (included in one of the sequences ($d_1$) to ($d_6$)) in combination with the specific sequences which have just been indicated. When there are several probes specific for the desired species, it is of course possible to use the combination of two such probes specific for this species.

For determining the presence or absence of Listeria monocytogenes, a system with two probes is used, in particular in a process characterized in that:

one of the probes has a sequence included in the sequence ($b_1$), ($b_{10}$), ($b_{14}$) or ($b_{15}$) and the other probe has a sequence included in the sequence ($b_4$), or one of the probes has a sequence included in the sequence ($c_1$), ($c_9$), ($c_{13}$) or ($c_{14}$) and the other included in the sequence ($c_4$).

The various oligonucleotides which have been defined above may also be used as nucleotide primers for the synthesis of a nucleic acid in the presence of a polymerase in a manner known per se, and in particular in amplification methods using such a synthesis in the presence of a polymerase (PCR, RT-PCR, and the like).

It is possible to use in particular the oligonucleotides of the invention as primers for the specific reverse transcription of a 23S ribosomal RNA sequence of at least one species or of at least one group of species of the genus Listeria in order to obtain a corresponding complementary DNA sequence. Such a reverse transcription may constitute the first stage of an RT-PCR, the next stage being the PCR amplification of the complementary DNA obtained. It is also possible to use these oligonucleotides as primers, in particular for the specific amplification, by polymerase chain reaction, of the rDNA sequence complementary to a 23S ribosomal RNA sequence of at least one species or of at least one group of species of the genus Listeria. The oligonucleotides defined above may also be used as therapy probes for treating infections caused by at least one species or one group of species of bacteria of the genus Listeria. These therapy probes, which are capable of hybridizing with the 23S ribosomal RNA and/or with the genomic DNA of the said bacteria may block the translation and/or transcription and/or replication phenomena. The principle of the methods of gene therapy is known and is based in particular on the use of a probe corresponding to an anti-sense strand: the formation of a hybrid between the probe and the sense strand is capable of disrupting at least one of the stages in deciphering the genetic information. The formation of a duplex between an oligonucleotide according to the invention and the 23S ribosomal RNA of the target bacteria is generally capable of disrupting the spatial configuration of the said rRNA and/or the combination of the said rRNA with the constituent proteins of the ribosome. The therapy probes can therefore be used as antibacterial drugs which make it possible to combat the infections caused by Listeria, including Listeria monocytogenes.

The following examples illustrate the invention.

EXAMPLE 1

Determination of the Nucleotide Sequence of the 23S Ribosomal RNA of Listeria

The nucleotide sequence of the DNA corresponding to the ribosomal RNA of the 23S subunit for the following species has been determined:

| L. monocytogenes | ATCC 19115 |
|---|---|
| L. innocua | ATCC 33090 |
| L. seeligeri | CCUG 15330 |
| Brochothrix thermosphacta | ATCC 11509 |

The sequencing was carried out according to the following steps: extraction of the DNA from the strains by the method of Sjöbring et al. (1990. Polymerase chain reaction for detection of *Mycobacterium tuberculosis*, J. Clin. Microbiol. 28 (10): 2200–2204), PCR amplification of the 23S ribosomal DNA by means of defined eubacterial primers in the phylogenetically conserved zones of this type of RNA. The pairs of eubacterial probes used, corresponding to sequences common to all bacteria, were the following:

```
a)  5' TCCGAATGGG GAAACCC 3'      positions 115-130  (SEQ ID NO:47)
    5' GATCTGGGCT GTTTC 3'        positions 988-1002 (SEQ ID NO:48)
b)  5' AAGAGGGAAA CARCCCAGA 3'    positions 982-1000 (SEQ ID NO:49)
    5' GGAACTTACC CGACAAGG 3'     positions 1963-1982 (SEQ ID NO:50)
c)  5' GAAATTCCTT GTCGGGT 3'      positions 1957-1975 (SEQ ID NO:51)
    5' CTAGGTCTGA CCTATCAAT 3'    positions 2864-2882 (SEQ ID NO:52)
```

It is Recalled that R Means: G or A

This step allowed the amplification of 3 zones of about 1 kb which make it possible to cover the whole of the 23S target and which were sequenced on each of the 2 strands by the chain termination method on an Applied Biosystems ABI 360 sequencer (Sanger et al., Proc. Natl. Acad. Sci. USA, 1977, 74: 5463–5467).

Three regions corresponding to the nucleotide sequences 664–728, 1188–1251 and 2209–2275 were then selected (reference to *L. monocytogenes* ATCC 19115; see annexes Table 1–3.

The 23S RNA of these regions was sequenced for various species and strains of Listeria and Brochothrix. The results are assembled in the table of sequences presented in Table 1–3.

EXAMPLE 2

Use of Probes Directed Against the 23S Ribosomal RNA of the Genus Listeria for the Specific Identification of *Listeria monocytogenes*

The following probe (complementary to a sequence in Table 2) was prepared;

ACGAACCTCT AAAGAG (SEQ ID NO:53)

This probe was used as detection probe in a sandwich hybridization test.

Another probe (complementary to a sequence in Table 3) was prepared:

TAAGCGTGGC GGGTTAGAAT (SEQ ID NO:54), and was used as capture probe in this test.

The 23S rRNA of a collection of Listeria strains and of other bacterial species (see below) was tested by hybridization by means of these two probes:

23 strains of *L. monocytogenes*, of varied serovars and origins 17 strains of *L. innocua*

8 strains of *L. seeligeri*

9 strains of *L. welshimeri*

16 strains of *L. ivanovii*

3 strains of *L. grayi*

4 strains of *L. murrayi*

2 strains of *Brochothrix thermosphacta*

1 strain of *Brochothrix campestris*

1 strain of *Bacillus subtilis*

1 strain of *Bacillus cereus*

1 strain of *Bacillus megaterium*

3 strains of *Erysepelothrix rhusiopathiae*

1 strain of *Lactobacillus acidophilus*

2 strains of Streptococcus group A 1 strain of Streptococcus group B 1 strain of Streptococcus group C 1 strain of *Streptococcus faecalis*

1 strain of *Streptococcus suis*

1 strain of *Escherichia coli*

The hybridization of the ribosomal RNAs of a target bacterium was carried out according to the semi-automated detection procedure described in French patent No. 2,663, 040. The detection probe is conjugated with alkaline phosphatase.

The ribosomal RNA of the strains was extracted according to the basic procedure for the extraction of RNA from Gram + bacteria described in "Current Protocols in Molecular Biology" 1987, Ausubel F M et al., Wiley intersicence, New York. A solution of 1 ng/μl of capture oligonucleotide, whose 5' end is coupled with the reagent Aminolink 2 (trade mark, Applied Biosystems, Foster City, Calif.) in 3×PBS (0.45 M NaCl; 0.15 M sodium phosphate; pH 7.0), is deposited in a microtitre plate (Nunc 439454). The plate is incubated for 2 h at 37° C. and then washed 3 times with 300 μl of PBST (1×PBS, Tween 20: 0.5% (Merck 822184)). The Aminolink 2 reagent makes it possible to add to the 5' end of the probe an arm comprising a 6-aminohexyl group. The use of a probe coupled to a ligand having a polar group (primary amine) passively attached to the support makes it possible to obtain an improved signal (application FR 2,679, 255).

The target (10 μl of total RNAs), mixed with 40 μl of PBS-salmon buffer (3×PBS+ salmon sperm DNA 10 μg/ml (Sigma D 9156) is deposited in the well in the presence of 50 μl of a solution of the oligonucleotide-peroxidase conjugate, constituting the detection probe, at the concentration of 0.1 ng/μl of oligonucleotide in a PBS-horse buffer (3×PBS+10% horse serum (BioMérieux 55842)). The plate is incubated for 1 h at 37° C. and then washed 3 times with 300 μl of PBST buffer. To each well are added 100 μl of OPD substrate (ortho-phenylene-diamine, Cambridge Medical Biotechnology ref./456) at a concentration of 4 mg/ml in a buffer (0.055 M citric acid, 0.1 M sodium monohydrogen phosphate, pH 4.93), to which 30% hydrogen peroxide diluted ¹⁄₁₀₀₀ is added immediately before use. After 20 min of reaction, the enzymatic activity is stopped with 100 μl of 1 N sulphuric acid and the reading is carried out at 492 nm on an Axia Microreader apparatus (AXIA) (bioMérieux).

The results of the tests carried out showed that the combination of probes used is specific for *L. monocytogenes*.

The specific combination of probes tested was adapted on the VIDAS automatic device (BIOMERIEUX-VITEX). The wall of the microplate well is here replaced with the SPR ("Solid Phase Receptacle") (BIOMERIEUX-VITEK-USA) which is a conical support made from a material called K resin (trade mark for a butadiene/styrene copolymer). The various reagents are deposited in a strip with several cuvettes and the various steps occur in the SPR which is capable of aspirating and discharging the reagents. The sandwich hybridization reaction described in the above procedure occurs on the internal wall of the cone.

In a first stage, the capture oligonucleotide comprising at its 5' end the Aminolink 2 ligand (Applied Biosystems-ref. 400808) is passively attached to the internal surface of the SPR, at a concentration of 1 ng/μl in a volume of 315 μl of a 4×PBS solution (200 mM sodium phosphate pH 7.0, 600 mM NaCl). After leaving overnight at room temperature or for two hours at 37° C., the cones are washed twice with a PBS-Tween solution and then dried under vacuum.

The strip associated with the VIDAS automatic device contains, in the cuvettes, the reagents necessary for the detection, that is to say:

in the first well of the strip, 10 μl of RNA extracted in the same buffer as for the microplate procedure above, in a second well, 200 μl of a solution at 0.1 ng/μl of the detection oligonucleotide-alkaline phosphatase conjugate, in a third and fourth well, 600 μl of PBS-Tween washing solution and finally a cuvette with 250 μl of MUP (4-methylumbelliferyl phosphate) substrate in solution in a diethanolamine buffer.

The contents of the first and second wells are aspirated into the pretreated cone as indicated above. After incubating for 30 minutes, the cone is washed twice with a PBS-Tween solution and 250 μl of MUP (4-methyl-umbelliferyl phosphate) substrate are aspirated and then discharged into a reading cuvette. The apparatus measures the fluorescent signal expressed in RFU (relative fluorescence units) in the cuvette.

The results obtained with this system are identical to those obtained in a microtitre plate.

EXAMPLE 3

In a similar manner, it is possible to detect the presence of *L. innocua* by means of the combination of the following two probes for capture and detection respectively:

```
1st probe: GGGTTAGAAT GGTCATACAG CCAGGGT (SEQ ID NO:54)

2nd probe: CCACGCGCTT AGCGTGG (SEQ ID NO:55)
```

EXAMPLE 4

In a similar manner, it is possible to detect the presence of *L. ivanovii* by means of the combination of the following two probes for capture and detection respectively:

```
1st probe: TTCATCCACA GTTTCGGTAA TATGT (SEQ ID NO:56)

2nd probe: CGAACCTCTA TAAGAGGTTC A (SEQ ID NO:57)
```

TABLE 1

| Sequence | Strain | ID |
|---|---|---|
| GGAGCCGT*AGCGAAA*GCGAGTCTGAATAGGGCG*CATAAGTAACAGGTCGTAGACCCGAAACCA*GG | L.monocyt ATCC 19115 | (SEQ ID NO:59) |
| ------------------------------------------------------------------------ | L.monocyt ATCC 15313 | |
| ------------------------------------------------------------------------ | L.monocyt D 011 | |
| ------------------------------------------------------------------------ | L.monocyt 83 09 022 | |
| ---------------------------------------A-------------------------------- | L.seelige CCUG 15330 | (SEQ ID NO:62) |
| ---N-----------------------------------A-------------------------------- | L.seelige 88 05 029 | (SEQ ID NO:64) |
| ---------------------------------------A-------------------------------- | L.seelige 88 06 080 | |
| ------------------------------------------------------------------------ | L.innocua ATCC 33090 | |
| ------------------------------------------------------------------------ | L.innocua 83 09 044 | |
| ------------------------------------------------------------------------ | L.innocua 83 09 005 | |
| ------------------------------------------------------------------------ | L.welshim CCUG 15529 | |

TABLE 1-continued

```
----------------------------------TATG------------------------- L.grayi A    ATCC 19120 (SEQ ID NO:68)
----------------------------------TATG------------------------- L.murrayi    CCUG 4984
--------------------------------*TAT----TTT-------------------- B.campest    ATCC 43754 (SEQ ID NO:70)
--------------------------------*T-T----TTT-------------------- B.thermos    ATCC 11509 (SEQ ID NO:73)
-------A---G-----C--------T-----------**-----TG----GTA------------C--- E.coli
```

TABLE 2

```
*AAACATATTACCGAAACTGTGGATGAACCTCTTTAGAG*GTTCGTG*GTAGGAGAGCGTTCTAA*GG* L.monocyt ATCC 19115 (SEQ ID NO:60)
--------------------------------------------------------------------- L.monocyt ATCC 15313
--------------------------------------------------------------------- L.monocyt D 011
--------------------------------------------------------------------- L.monocyt 83 09 022
--------------------------------------------------------------------- L.seelige CCUG 15330
--------------------------------------------------------------------- L.seelige 88 05 028
--------------------------------------------------------------------- L.seelige 88 05 029
--------------------------------------------------------------------- L.seelige 88 06 080
--------------------------------CG----------------------------------- L.innocua ATCC 33090 (SEQ ID NO:65)
--------------------------------CG----------------------------------- L.innocua 83 09 044
--------------------------------CG----------------------------------- L.innocua 83 09 005
--------------------------------ATAGAG------------------------------- L.ivanovi 88 05 019 (SEQ ID NO:67)
--------------------------------CG----------------------------------- L.welshim CCUG 15529
-----G----------------------A----CG--T------------------------------- L.grayi A  ATCC 19120 (SEQ ID NO:69)
-----G----------------------A----CG--T------------------------------- L.murrayi  CCUG 4984
---------------G---------TGT---T-GG-C-A-*****------------------------ B.campest  ATCC 43754 (SEQ ID NO:72)
---------------G---------TGT--GTAGG-C-A-*****------------------------ B.thermos  ATCC 11509 (SEQ ID NO:75)
-----CATGC------G---C--CA-CGA-G---AT-C*----GT--G*GTA-G-GAGCG-TCT*GTAA E.coli
```

TABLE 3

```
ACCCTGGCTGT*ATGACCATTCTAACCCGCCACGCTTAGCGCGTGGGGAGACAGTGTCAGGTGGGC*AG L.monocyt ATCC 19115 (SEQ ID NO:61)
---------------------------------------------------------------------- L.monocyt ATCC 15313
---------------------------------------------------------------------- L.monocyt D 011
---------------------------------------------------------------------- L.monocyt 83 09 030
---------------------------------------------------------------------- L.monocyt 83 09 022
---------------------------A------------------------------------------ L.seelige CCUG 15330 (SEQ ID NO:63)
---------------------------A------------------------------------------ L.seelige 88 05 028
---------------------------A------------------------------------------ L.seelige 88 05 029
---------------------------A-----------A------------------------------ L.seelige 88 06 080
-----------------------------------A---------------------------------- L.innocua ATCC 33090 (SEQ ID NO:66)
-----------------------------------A---------------------------------- L.innocua 83 09 044
-----------------------------------A---------------------------------- L.innocua 83 09 005
-----------------------------------A---------------------------------- L.innocua 83 09 014
---------------------------------------------------------------------- L.ivanovi CIP 7842
---------------------------------------------------------------------- L.welshim CCUG 15529
---------------------------------------------------------------------- L.grayi A  ATCC 19120
---------------------------------------------------------------------- L.murrayi  CCUG 4984
-----A-------G-TGG-T------------AC-A----T--T-GT----------------C------ B.campest  ATCC 43754 (SEQ ID NO:72)
-----A-------G-TGG-T------------AC-A----T--T-GT---------------------- B.thermos  ATCC 11509 (SEQ ID NO:75)
-----TTAATG-T-TGATG--------GTTGAC-CG-A-T-CG-GTT-CG---------T------T--- E.coli
```

We claim:

1. A single-stranded oligonucleotide consisting of a sequence included in an oligonucleotide selected from the group consisting of oligonucleotides of SEQ ID NOS: 1–3 and 5–11 and oligonucleotides fully complementary to said oligonucleotides of SEQ ID NOS: 1–3 and 5–11, wherein said sequence has at least 12 nucleotide units.

2. An oligonucleotide according to claim 1, consisting of a sequence included in an oligonucleotide selected from the group consisting of oligonucleotides of SEQ ID NOS: 27–40 and oligonucleotides fully complementary to said SEQ ID NOS: 27–40.

3. An oligonucleotide according to claim 1, consisting of a sequence included in an oligonucleotide selected from the group consisting of oligonucleotides of SEQ ID NOS: 41–46 and oligonucleotides fully complementary to said SEQ ID NOS:41–46.

4. An oligonucleotide according to claim 1, wherein said oligonucleotide is immobilized on a solid support.

5. An oligonucleotide according to claim 1, wherein said oligonucleotide is labeled with a tracer.

6. A process for determining the presence or absence of at least one bacterium of the genus Listeria in a sample suspected of containing nucleic acids of at least one said bacterium, comprising:

contacting said sample with at least one nucleic acid probe; and determining whether a hybridization complex is formed between said at least one nucleic acid probe and said nucleic acids of said sample, wherein said at least one nucleic acid probe comprises an oligonucleotide according to claim 1, and whereby when a hybridization complex is formed, said at least one bacterium of the genus Listeria is present.

7. A process for determining the presence or absence of at least one bacterium of the genus Listeria in a sample suspected of containing nucleic acids of at least one said bacterium comprising:

contacting said sample with two nucleic acid probes; and determining whether a hybridization complex is formed between said probes and said nucleic acids of said sample, wherein each of said probes comprises an oligonucleotide according to claim 19;

wherein said probes hybridize with non-overlapping regions of the 23S rRNA of a bacterium of the genus Listeria or its complement; and whereby when said hybridization complex is formed, said at least one bacterium of the genus Listeria is present.

8. A process according to claim 7, wherein at least one of said probes comprises a sequence included in an oligonucleotide selected from the group consisting of oligonucleotides of SEQ ID NOS: 27–40 and oligonucleotides fully complementary to said oligonucleotides of SEQ ID NOS: 27–40.

9. A process according to claim 7, wherein one of said nucleic acid probes is immobilized on a solid support and the other said nucleic acid probe is labeled with a tracer.

10. A process according to claim wherein said at least one nucleic acid probe comprises a sequence included in an oligonucleotide selected from the group consisting of oligonucleotides of SEQ ID NOS: 41–46 and oligonucleotides fully complementary to said oligonucleotide of SEQ ID NOS: 41–46.

11. An oligonucleotide according to claim 1, wherein said oligonucleotide comprises a sequence of at least five consecutive nucleotide units of a sequence between the parentheticals of a sequence selected from the group consisting of:

```
AGTCTGAATA GG(GCGCATA)A GTAACAGGTC GTAGA (SEQ ID NO:12),

AGTCTGAATA GG(GCGAATA)A GTAACAGGTC GTAGA (SEQ ID NO:13),

AGTCTGAATA GG(GCGTATGA AG)TAACAGGT CGTAGA (SEQ ID NO:14),

CCGAAACTGT GGATGAACCT (CTTTAGAG)GT TCGTGGTAGG (SEQ ID NO:15),

CCGAAACTGT GGATGAACCT (CTTCGGAG)GT TCGTGGTAGG (SEQ ID NO:16),

CCGAAACTGT GGATGAACCT (CTTATAGAGG) TTCGTGGTAG G (SEQ ID NO:17),

CCGAAACTGT GGATGAACAT CTT(CGGATGT T)CGTGGTAGG (SEQ ID NO:18),
```

-continued

A(AACGTAT)TA CCGAAACTGT GGATGAA (SEQ ID NO:19),

CCGAAACTGT GGATG(AACAT CT)TCGGATGT TCGTGGTAGG (SEQ ID NO:20),

TGGCTGTATG ACCATTCTAA (CCCGCCA)CGC T (SEQ ID NO:21),

CCAC(GCTTAG C)GCGTGGGGA GACAGTGTCA GG (SEQ ID NO:22),

TGGCTGTATG ACCATTCTAA (CCCACCA)CGC TTAGCGCGTG GGAGACAGT GTCAGG (SEQ ID NO:23),

TGGCTGTATG ACCATTCTAA CCCGCCAC(GC TAAGC)GCGTG GGGAGACAGT GTCAGG (SEQ ID NO:24), (CCGCCA)CGCT TAGCGCGTGG GGAGACAGTG TCAGGTGGGC AG (SEQ ID NO:25),

TGGCTGTATG ACCATTCTAA CCCGCCAC(GC TTAG)(SEQ ID NO.26), and and sequences fully complementary to SEQ ID NOS: 12–26.

12. A process according to claim 7, wherein at least one of said nucleic acid probes comprises a sequence of at least five consecutive nucleotide units of a sequence between the parentheticals of a sequence selected from the group consisting of:

AGTCTGAATA GG(GCGCATA)A GTAACAGGTC GTAGA (SEQ ID NO:12),

AGTCTGAATA GG(GCGAATA)A GTAACAGGTC GTAGA (SEQ ID NO:13),

AGTCTGAATA GG(GCGTATGA AG)TAACAGGT CGTAGA (SEQ ID NO:14),

CCGAAACTGT GGATGAACCT (CTTTAGAG)GT TCGTGGTAGG (SEQ ID NO:15),

CCGAAACTGT GGATGAACCT (CTTCGGAG)GT TCGTGGTAGG (SEQ ID NO:16),

CCGAAACTGT GGATGAACCT (CTTATAGAGG) TTCGTGGTAG G (SEQ ID NO:17),

CCGAAACTGT GGATGAACAT CTT(CGGATGT T)CGTGGTAGG (SEQ ID NO:18),

A(AACGTAT)TA CCGAAACTGT GGATGAA (SEQ ID NO:19),

CCGAAACTGT GGATG(AACAT CT)TCGGATGT TCGTGGTAGG (SEQ ID NO:20),

TGGCTGTATG ACCATTCTAA (CCCGCCA)CGC T (SEQ ID NO:21),

CCAC(GCTTAG C)GCGTGGGGA GACAGTGTCA GG (SEQ ID NO:22),

TGGCTGTATG ACCATTCTAA (CCCACCA)CGC TTAGCGCGTG GGAGACAGT GTCAGG (SEQ ID NO:23),

TGGCTGTATG ACCATTCTAA CCCGCCAC(GC TAAGC)GCGTG GGGAGACAGT GTCAGG (SEQ ID NO:24), (CCGCCA)CGCT TAGCGCGTGG GGAGACAGTG TCAGGTGGGC AG (SEQ ID NO:25),

TGGCTGTATG ACCATTCTAA CCCGCCAC(GC TTAG) (SEQ ID NO.26), and sequences fully complementary to said SEQ ID NOS: 12–26.

13. A process according to claim 6, wherein said at least one nucleic acid probe comprises:

a sequence of at least five consecutive nucleotide units of a sequence between the parentheticals of a sequence selected from the group consisting of:

AGTCTGAATA GG(GCGAATA)A GTAACAGGTC GTAGA (SEQ ID NO:13),

TGGCTGTATG ACCATTCTAA (CCCACCA)CGC TTAGCGCGTG GGAGACAGT GTCAGG (SEQ ID NO:23), and sequences fully complementary to said SEQ ID NO: 13 and SEQ ID NO: 23; or a sequence included in an oligonucleotide selected from the group consisting of oligonucleotides of SEQ ID NO: 28, SEQ ID NO: 36 and oligonucleotides fully complementary to said oligonucleotides SEQ ID NO: 28 and SEQ ID NO: 36.

14. A process according to claim 6, wherein said at least one nucleic acid probe comprises;

a sequence of at least five consecutive nucleotide units of a sequence between the parentheticals of a sequence selected from the group consisting of:

TGGCTGTATG ACCATTCTAA CCCGCCAC(GC TAAGC)GCGTG GGGAGACAGT GTCAGG (SEQ ID NO: 24), and oligonucleotides fully complementary to said SEQ ID NO: 24; or a sequence included in an oligonucleotide selected from the group consisting of oligonucleotides of SEQ ID NO: 38 or oligonucleotides fully complementary to said oligonucleotide of SEQ ID NO: 38.

15. A process according to claim 6, wherein said at least one nucleic acid probe comprises:

a sequence of at least five consecutive nucleotide units of a sequence between the parentheticals of a sequence selected from the group consisting of:

CCGAAACTGT GGATGAACCT (CTTATAGAGG) TTCGTGGTAG G (SEQ ID NO: 17), and oligonucleotides fully complementary to said SEQ ID NO: 17; or a sequence included in an oligonucleotide selected from the group consisting of oligonucleotides of SEQ ID NO: 32 or oligonucleotides complementary to said oligonucleotide of SEQ ID NO: 32.

16. A process according to claim 6, wherein said at least one nucleic acid probe comprises:

a sequence of at least five consecutive nucleotide units of a sequence between the parentheticals of a sequence selected from the group consisting of:

18. A method for synthesizing complementary copies of ribosomal RNA or DNA of a bacterium of the genus Listeria, by extension of a primer under the action of a nucleic acid polymerase, comprising:

hybridizing a primer comprising an oligonucleotide according to claim 19 to a target ribosomal RNA or DNA, and extending said primer in the presence of said polymerase.

19. An oligonucleotide according claim 1, wherein said single-stranded oligonucleotide comprises up to 35 nucleotide units.

20. A process according to claim 13, wherein said at least one nucleic acid probe is used in combination with a probe comprising a sequence included in an oligonucleotide selected from the group consisting of oligonucleotides of SEQ ID NOS: 41–46 and oligonucleotides fully complementary to said oligonucleotides of SEQ ID NOS: 41–46.

21. A process according to claim 14, wherein said at least none nucleic acid probe is used in combination with a probe comprising a sequence included in an oligonucleotide selected from the group consisting of oligonucleotides of SEQ ID NOS: 41–46 and oligonucleotides fully complementary to said oligonucleotides of SEQ ID NOS: 41–46.

22. A process according to claim 15, wherein said at least one nucleic acid probe is used in combination with a probe

```
AGTCTGAATA GG(GCGTATGA AG)TAACAGGT CGTAGA (SEQ ID NO:14),

CCGAAACTGT GGATGAACAT CTT(CGGATGT T)CGTGGTAGG (SEQ ID NO:18),

A(AACGTAT)TA CCGAAACTGT GGATGAA (SEQ ID NO:19),

CCGAAACTGT GGATG(AACAT CT)TCGGATGT TCGTGGTAGG (SEQ ID NO:20),
``` and oligonucleotides fully complementary to said SEQ ID NO: 14, SEQ ID NO: 18, SEQ ID NO: 19 and SEQ ID NO: 20; or a sequence included in an oligonucleotide selected from the group consisting of oligonucleotides of SEQ ID NO: 29, SEQ ID NO: 33, SEQ ID NO: 34 and oligonucleotides fully complementary to oligonucleotide of SEQ ID NO: 29, SEQ ID NO: 33 and SEQ ID NO: 34.

17. A process according to claim 6, wherein said nucleic acid probes include:

a probe comprising a sequence of at least five consecutive nucleotide units of a sequence between the parentheticals of a sequence selected from the group consisting of:

comprising a sequence included in an oligonucleotide selected from the group consisting of oligonucleotides of SEQ ID NOS: 41–46 and oligonucleotides fully complementary to said oligonucleotides of SEQ ID NOS: 41–46.

23. A process according to claim 16, wherein said at least one nucleic acid probe is used in combination with a probe comprising a sequence included in an oligonucleotide selected from the group consisting of oligonucleotides of SEQ ID NOS: 41–46 and oligonucleotides fully complementary to said oligonucleotides of SEQ ID NOS: 41–46.

24. A process according to claim 7, wherein said at least two nucleic acid probes include:

a probe comprising a sequence included in an oligonucleotide selected from the group consisting of SEQ ID NO: 27, SEQ ID NO: 35, SEQ ID NO: 39, SEQ ID NO: 40 and oligonucleotides complementary to said oligo-

```
AGTCTGAATA GG(GCGCATA)A GTAACAGGTC GTAGA (SEQ ID NO:12),

TGGCTGATATG ACCATTCTAA (CCCGCCA)CGC T (SEQ ID NO:21), (CCGCCA)CGCT TAGCGCGTGG GGAGACAGTG TCAGGTGGGC AG (SEQ ID NO:25),

TGGCTGTATG ACCATTCTAA CCCGCCAC(GC TTAG) (SEQ ID NO.26),
``` and oligonucleotides fully complementary to said SEQ ID NO: 12, SEQ ID NO: 21, SEQ ID NO: 25 and SEQ ID NO: 26; and a probe comprising a sequence of at least five consecutive nucleotide units of a sequence between the parentheticals in CCGAAACTGT GGATGAACCT (CTTTAGAG)GT TCGTGGTAGG (SEQ ID NO: 15), or oligonucleotides fully complementary to said SEQ ID NO: 15.

nucleotides of SEQ ID NO: 27, SEQ ID NO: 35, SEQ ID NO: 39 and SEQ ID NO: 40; and a probe comprising a sequence included in an oligonucleotide selected from the group consisting of SEQ ID NO: 30 or oligonucleotides complementary to said SEQ ID NO: 30.

* * * * *